(12) United States Patent
Gilder et al.

(10) Patent No.: US 10,534,816 B2
(45) Date of Patent: *Jan. 14, 2020

(54) ASSOCIATION OF ENTITY RECORDS BASED ON SUPPLEMENTAL TEMPORAL INFORMATION

(71) Applicant: International Business Machines Corporation, Armonk, NY (US)

(72) Inventors: Jason R. Gilder, Cleveland Heights, OH (US); Anil K. Jain, Solon, OH (US); Jacob O. Miller, Cleveland, OH (US); Matthew M. Pohlman, University Heights, OH (US)

(73) Assignee: International Business Machines Corporation, Armonk, NY (US)

( * ) Notice: Subject to any disclaimer, the term of this patent is extended or adjusted under 35 U.S.C. 154(b) by 227 days.

This patent is subject to a terminal disclaimer.

(21) Appl. No.: 15/819,183

(22) Filed: Nov. 21, 2017

(65) Prior Publication Data

US 2018/0075030 A1 Mar. 15, 2018

Related U.S. Application Data

(63) Continuation of application No. 14/988,001, filed on Jan. 5, 2016, now Pat. No. 9,864,746.

(51) Int. Cl.
*G06F 16/93* (2019.01)
*G16H 10/60* (2018.01)
*G06Q 10/06* (2012.01)

(52) U.S. Cl.
CPC ............ *G06F 16/93* (2019.01); *G16H 10/60* (2018.01); *G06Q 10/06* (2013.01)

(58) Field of Classification Search
CPC ..................................................... G06Q 10/06
See application file for complete search history.

(56) References Cited

U.S. PATENT DOCUMENTS

| 6,523,019 | B1 | 2/2003 | Borthwick | |
| 8,438,182 | B2 * | 5/2013 | Gillam | G16H 10/60 707/780 |

(Continued)

OTHER PUBLICATIONS

Fellegi, Ivan P., and Alan B. Sunter. "A theory for record linkage." Journal of the American Statistical Association 64.328 (1969): 1183-1210.

(Continued)

*Primary Examiner* — Neal Sereboff
(74) *Attorney, Agent, or Firm* — Ryan Lewis; Edell, Shapiro & Finnan, LLC

(57) ABSTRACT

A system links data objects associated with a common entity and includes at least one processor. The system compares data objects within one or more source systems to identify candidate data objects associated with a corresponding common entity based on information within those data objects. The candidate data objects are analyzed based on supplemental temporal information within the one or more source systems pertaining to the candidate data objects to determine resulting data objects associated with the corresponding common entity. The resulting data objects are linked to form a set of data objects for the common entity. Embodiments of the present invention further include a method and computer program product for linking data objects associated with a common entity.

20 Claims, 12 Drawing Sheets

(56) References Cited

U.S. PATENT DOCUMENTS

| | | |
|---|---|---|
| 8,495,069 B2 | 7/2013 | Friedlander et al. |
| 2003/0126156 A1 | 7/2003 | Stoltenberg et al. |
| 2005/0154368 A1* | 7/2005 | Lim .................. A61M 5/178 |
| | | 604/403 |
| 2006/0179050 A1 | 8/2006 | Giang et al. |
| 2011/0246237 A1* | 10/2011 | Vdovjak ............. G06Q 50/24 |
| | | 705/3 |
| 2013/0080192 A1* | 3/2013 | Bucur ................ G06Q 50/24 |
| | | 705/3 |
| 2014/0032240 A1 | 1/2014 | Lougheed et al. |
| 2014/0101172 A1* | 4/2014 | Dua .................. G06F 16/25 |
| | | 707/750 |
| 2017/0192967 A1 | 7/2017 | Gilder |

OTHER PUBLICATIONS

Jaro, M. A., Probabilistic linkage of large public health data files. Statist. Med., 14: 491-498. doi: 10.1002/sim.4780140510. (1995).

"The Explorys Platform", IBM Watson Health, Solution Brief, Produced in the United States of America Nov. 2015, 4 pages.

List of IBM Patents or Patent Applications Treated as Related, Nov. 2017, 1 page.

* cited by examiner

| VERTEX | ADJACENCIES | ASSIGNED GROUP ID | ACTIVATED |
|--------|-------------|-------------------|-----------|
| 1 | 2, 3 | 1 | TRUE |
| 2 | 1, 4 | 1 | TRUE |
| 3 | 1 | 1 | TRUE |
| 4 | 2 | 2 | TRUE |
| 5 | 6 | 5 | TRUE |
| 6 | 5, 7 | 5 | TRUE |
| 7 | 6, 8 | 6 | TRUE |
| 8 | 7, 9 | 7 | TRUE |
| 9 | 8 | 8 | TRUE |

| VERTEX | ADJACENCIES | ASSIGNED GROUP ID | ACTIVATED |
|--------|-------------|-------------------|-----------|
| 1 | 2, 3 | 1 | FALSE |
| 2 | 1, 4 | 1 | FALSE |
| 3 | 1 | 1 | FALSE |
| 4 | 2 | 1 | TRUE |
| 5 | 6 | 5 | FALSE |
| 6 | 5, 7 | 5 | FALSE |
| 7 | 6, 8 | 5 | TRUE |
| 8 | 7, 9 | 6 | TRUE |
| 9 | 8 | 7 | TRUE |

| VERTEX | ADJACENCIES | ASSIGNED GROUP ID | ACTIVATED |
|--------|-------------|-------------------|-----------|
| 1 | 2, 3 | 1 | FALSE |
| 2 | 1, 4 | 1 | FALSE |
| 3 | 1 | 1 | FALSE |
| 4 | 2 | 1 | FALSE |
| 5 | 6 | 5 | FALSE |
| 6 | 5, 7 | 5 | FALSE |
| 7 | 6, 8 | 5 | FALSE |
| 8 | 7, 9 | 5 | TRUE |
| 9 | 8 | 6 | TRUE |

| VERTEX | ADJACENCIES | ASSIGNED GROUP ID | ACTIVATED |
|---|---|---|---|
| 1 | 2, 3 | 1 | FALSE |
| 2 | 1, 4 | 1 | FALSE |
| 3 | 1 | 1 | FALSE |
| 4 | 2 | 1 | FALSE |
| 5 | 6 | 5 | FALSE |
| 6 | 5, 7 | 5 | FALSE |
| 7 | 6, 8 | 5 | FALSE |
| 8 | 7, 9 | 5 | FALSE |
| 9 | 8 | 5 | TRUE |

| VERTEX | ADJACENCIES | ASSIGNED GROUP ID | ACTIVATED |
|---|---|---|---|
| 1 | 2, 3 | 1 | FALSE |
| 2 | 1, 4 | 1 | FALSE |
| 3 | 1 | 1 | FALSE |
| 4 | 2 | 1 | FALSE |
| 5 | 6 | 5 | FALSE |
| 6 | 5, 7 | 5 | FALSE |
| 7 | 6, 8 | 5 | FALSE |
| 8 | 7, 9 | 5 | FALSE |
| 9 | 8 | 5 | FALSE |

ASSOCIATION OF ENTITY RECORDS BASED ON SUPPLEMENTAL TEMPORAL INFORMATION

CROSS-REFERENCE TO RELATED APPLICATIONS

This application is a continuation of U.S. patent application Ser. No. 14/988,001, entitled "Association of Entity Records Based on Supplemental Temporal Information" and filed on Jan. 5, 2016, the disclosure of which is incorporated herein by reference in its entirety.

BACKGROUND

1. Technical Field

Present invention embodiments relate to data matching systems, and more specifically, data matching systems utilizing supplemental temporal information, such as temporal clinical information.

2. Discussion of the Related Art

Healthcare networks have very complicated organization structures. An organization typically comprises multiple source systems (e.g., a source of electronic medical records including electronic health records (EHR), records from a claims system, lab feed, various data sources implementing the HL7 standard, patient satisfaction survey, etc.). Within each source system, data may be input for various entities (i.e., patients, companies, etc.), perhaps based on forms that a patient fills out. Accordingly, various data objects in a source system may be associated with a common entity (i.e., patients) even though the data objects have different information contained therein. For example, data objects within different source systems of an organization or even within a single source system of a single organization may be associated with a common patient.

Moreover, clinically integrated networks (CIN) or galaxies (e.g., a group of organizations) are collections of individual healthcare systems with data sharing agreements. Data governance restrictions may exist within organizations or galaxies (e.g., not all data can be shared with all providers). Accordingly, examining and associating records of the different healthcare systems with common entities may be complex, burdensome, and processing intensive (with respect to processing resources and processing time). This is typically exacerbated in the case of data governance restrictions.

SUMMARY

According to one embodiment of the present invention, a system links data objects associated with a common entity and includes at least one processor. The system compares data objects within one or more source systems to identify candidate data objects associated with a corresponding common entity based on information within those data objects. The candidate data objects are analyzed based on supplemental temporal information within the one or more source systems pertaining to the candidate data objects to determine resulting data objects associated with the corresponding common entity. The resulting data objects are linked to form a set of data objects for the common entity. Embodiments of the present invention further include a method and computer program product for linking data objects associated with a common entity.

BRIEF DESCRIPTION OF THE DRAWINGS

Generally, like reference numerals in the various figures are utilized to designate like components.

FIGS. 8B-8F are illustrations of example connection tables for applying a connected components process to the graphical representation of FIG. 8A according to an embodiment of the present invention.

DETAILED DESCRIPTION

An organization may comprise multiple source systems (e.g., a source of electronic medical records including electronic health records (EHR), records from a claims system, lab feed, various data sources implementing the HL7 standard, patient satisfaction survey, etc.), while clinically integrated networks (CIN) or galaxies (e.g., a group of organizations) are collections of individual healthcare systems with data sharing agreements. Present invention embodiments primarily pertain to patient or other entity matching at a source system level and use supplemental temporal information, such as medical information that only has meaning when considered in context of the time or order of the information to properly link or split data objects (i.e., patient records). However, in some embodiments, present invention embodiments could be used to determine entity matches within an organization, entity matches within a galaxy, or entity matches between galaxies if desired.

Present invention embodiments provide several advantages. For example, a present invention embodiment supports or improves patient matching within a source system by allowing linking or splitting of data objects where static information would not recognize an association or disassociation. In other words, present invention embodiments may increase the effectiveness and accuracy of associating data objects with a common entity. Increasing the effectiveness and accuracy of matching may, in turn, support complex data governance issues of an organization or galaxy.

The entity matching is preferably implemented in a distributed computing environment as described below, and is highly scalable to hundreds of millions of patients or other entities. By way of example, 150 million source persons may be processed into 95 million resolved persons in a short time interval (e.g., a couple of hours, etc.). However, present invention embodiments are environment agnostic and may be implemented in non-distributed computing environments if desired.

Figure 1:
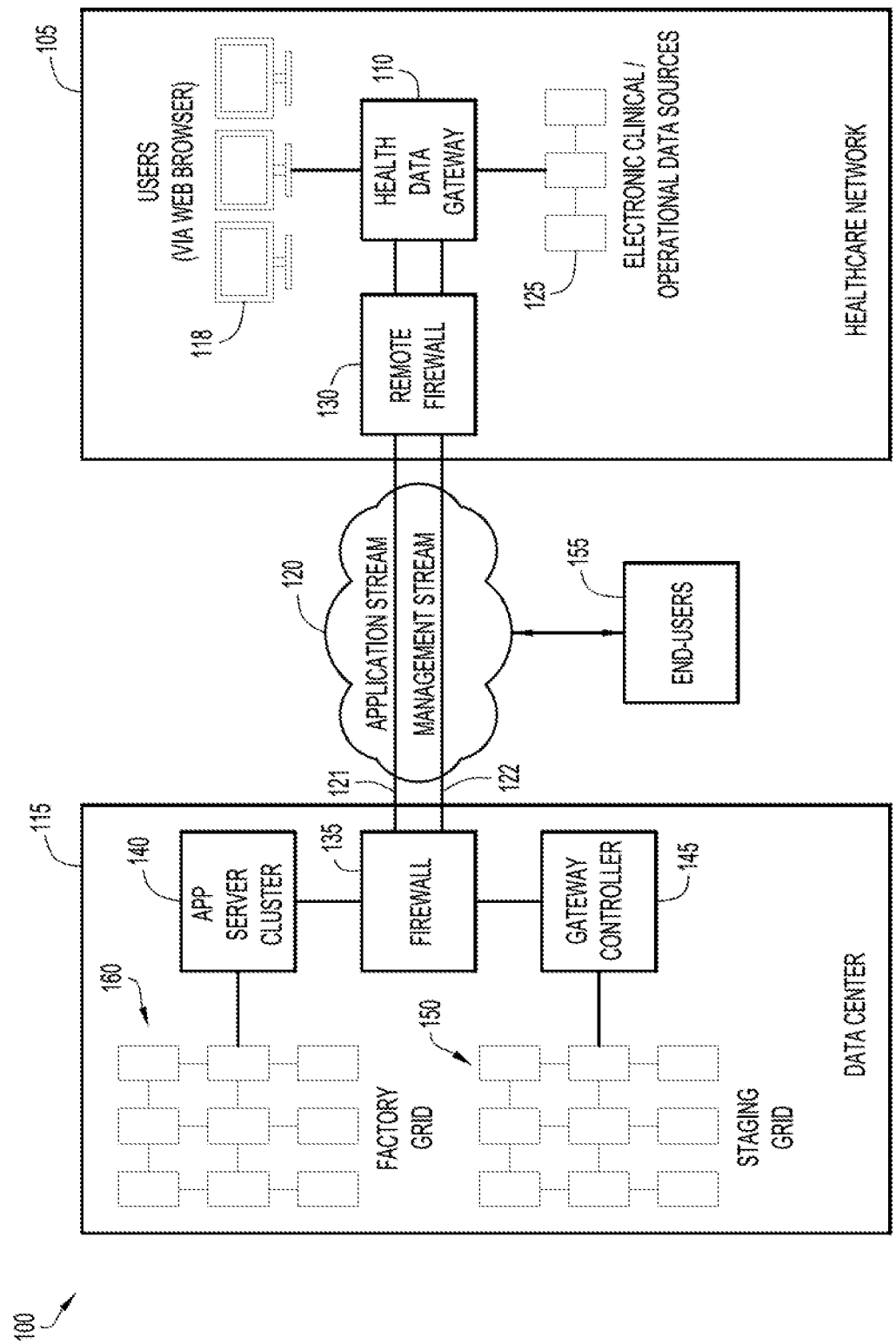
FIG. 1 is a diagrammatic illustration of an example computing environment according to an embodiment of the present invention.

An example computing environment for use with present invention embodiments is illustrated in FIG. 1. Computing environment 100 includes a healthcare network 105 in communication with a data center 115 over a communications network 120 (e.g., providing a secure virtual private network (VPN)). The communications over network 120 preferably occur between a firewall 130 of healthcare network 105 and a firewall 135 of data center 115. The communications over network 120 may include an application stream 121 pertaining to communications for applications and a management stream 122 pertaining to communications for managing the data. The network may be implemented by any number of any suitable communications media (e.g., wide area network (WAN), local area network (LAN), Internet, Intranet, etc.). Alternatively, healthcare network 105 and data center 115 may be local to each other, and communicate via any appropriate local communication medium (e.g., local area network (LAN), hardwire, wireless link, Intranet, etc.).

Healthcare network 105 includes a health data gateway 110 coupled to end-user systems 118 and one or more clinical/operational data sources 125 providing various medical information (e.g., electronic health records (EHR), records from a claims system, lab feed, various data sources implementing the HL7 standard, patient satisfaction survey, etc.) stored according to a source data model.

Data center 115 includes an application server cluster 140, a gateway controller 145, a staging grid 150, and a factory grid 160. Health data gateway 110 of healthcare network 105 is configured to acquire data from data sources 125 and transmit the acquired data to gateway controller 145 of data center 115. The gateway controller receives the incoming data from the communications network and processes that data to staging grid 150. The staging and factory grids each include a cluster of computer systems to store data and perform parallel processing. By way of example, the staging and factory grids each employ a HADOOP cluster with a HADOOP distributed file system (HDFS).

Staging grid 150 inspects and publishes the data to factory grid 160 in accordance with a data model employed by the factory grid. Factory grid 160 includes various engines to perform desired analytics on the data based on queries received from end-user systems 118 and other end-user systems 155 accessing data center 115 over network 120. The queries are handled in conjunction with application server cluster 140 to produce desired results.

Figure 2:
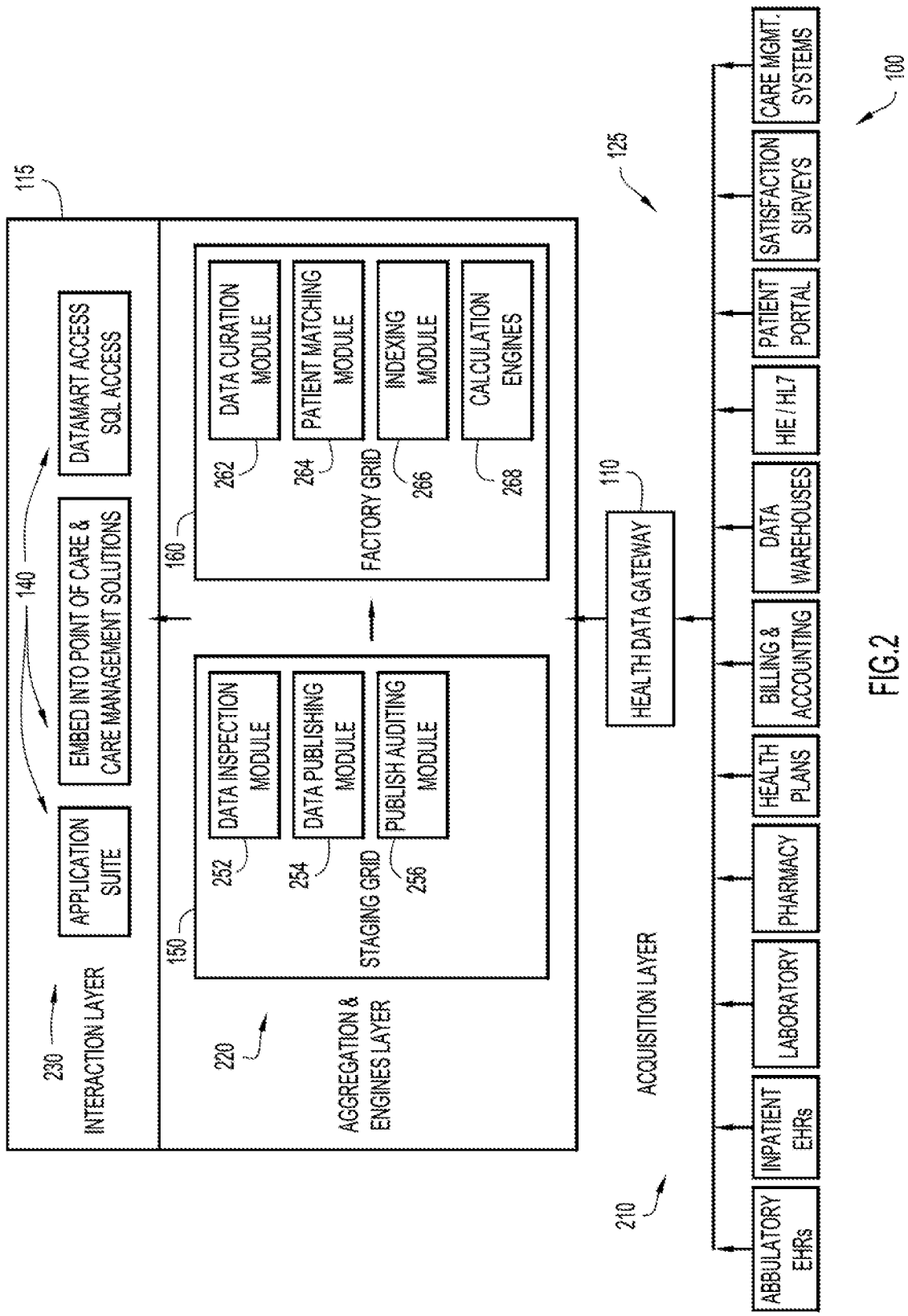
FIG. 2 is a diagrammatic illustration of the data center of the computing environment of FIG. 1 according to an embodiment of the present invention.

Referring to FIG. 2, health data gateway 110 of one or more healthcare networks is configured to acquire data from data sources 125 of those healthcare networks (e.g., ambulatory electronic health records (EHR), inpatient electronic health records (EHR), laboratory data, pharmacy data, health plan data, billing and accounting data, data warehouses, health information exchange (HIE)/HL7 data, patient portal, satisfaction surveys, care management systems, etc.) and transmit the acquired data to gateway controller 145 of data center 115 as described above. The healthcare networks and/or data sources 125 form an acquisition layer 210 providing data to data center 115 via health data gateway 110.

Gateway controller 145 receives the incoming data from communications network 120 and processes that data to staging grid 150 employing data models of the source systems. Staging grid 150 includes a data inspection module 252, a data publishing module 254, and a publish auditing module 256 to inspect, publish, and audit the data to factory grid 160 in accordance with the data model employed by the factory grid.

Factory grid 160 includes a data curation module 262, a patient matching module 264, an indexing module 266, and various calculation/analytic engines 268. Data curation module 262 performs data curation operations including mapping codes, data cleansing, and standardization, while patient matching module 264 performs patient matching operations to determine records associated with the same patient. Indexing module 266 performs indexing operations including combining records based on patient matching, mappings, and application of risk models. The calculation/analytic engines perform the desired analytics based on queries received from end-users from an interaction layer 230 enabling application server cluster 140 to provide various applications for processing and accessing the data (e.g., analytic applications, SQL access, etc.). The staging and factory grids form an aggregation and engines layer 220 to process the acquired data, while the queries are handled by factory grid 160 in conjunction with application server cluster 140 to produce desired results for the interaction layer.

The various applications of application server cluster 140 may be provided in a cloud environment. It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones or other devices, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly release to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

Figure 3:
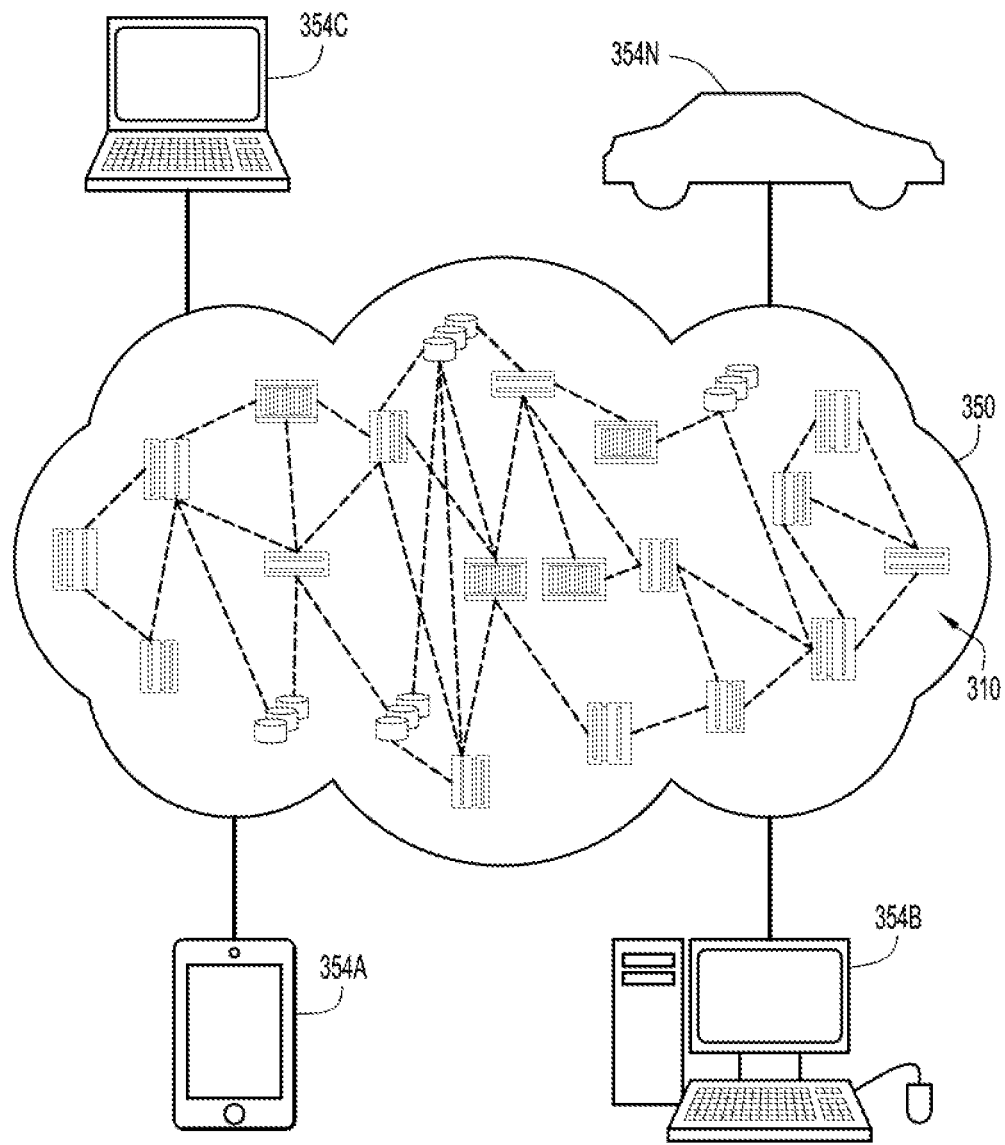
FIG. 3 is a diagrammatic illustration of an example cloud computing environment for the computing environment of FIG. 1 according to an embodiment of the present invention.

A cloud computing environment is service oriented with a focus on statelessness, low coupling, modularity, and semantic interoperability. At the heart of cloud computing is an infrastructure comprising a network of interconnected nodes. Referring now to FIG. 3, illustrative cloud computing environment 350 is depicted. As shown, cloud computing environment 350 comprises one or more cloud computing nodes 310 with which local computing devices used by cloud consumers, such as, for example, personal digital assistant (PDA) or cellular telephone 354A, desktop computer 354B, laptop computer 354C, and/or automobile computer system 354N may communicate. Nodes 310 may communicate with one another. They may be grouped (not shown) physically or virtually, in one or more networks, such as Private, Community, Public, or Hybrid clouds as described hereinabove, or a combination thereof. This allows cloud computing environment 350 to offer infrastructure, platforms and/or software as services for which a cloud consumer does not need to maintain resources on a local computing device. It is understood that the types of computing devices 354A-N shown in FIG. 3 are intended to be illustrative only and that computing nodes 310 and cloud computing environment 350 can communicate with any type of computerized device over any type of network and/or network addressable connection (e.g., using a web browser).

Figure 4:
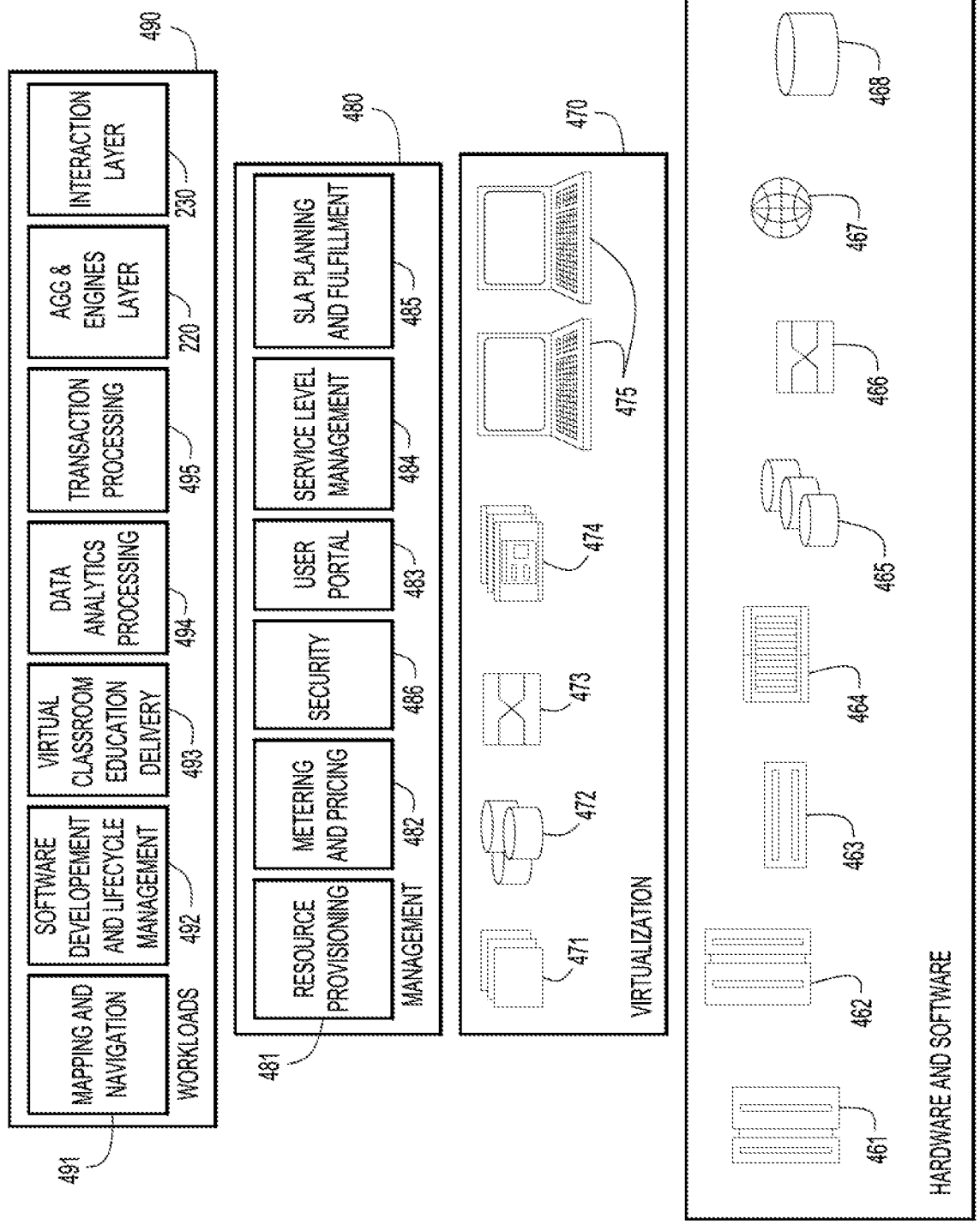
FIG. 4 is a diagrammatic illustration of abstraction model layers according to an embodiment of the present invention.

Referring now to FIG. 4, a set of functional abstraction layers provided by cloud computing environment 350 (FIG. 3) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 460 includes hardware and software components. Examples of hardware components include: mainframes 461; RISC (Reduced Instruction Set Computer) architecture based servers 462; servers 463; blade servers 464; storage devices 465; and networks and networking components 466. In some embodiments, software components include network application server software 467 and database software 468.

Virtualization layer 470 provides an abstraction layer from which the following examples of virtual entities may be provided: virtual servers 471; virtual storage 472; virtual networks 473, including virtual private networks; virtual applications and operating systems 474; and virtual clients 475.

In one example embodiment, management layer 480 may provide some or all of the functions for data center 115 described herein. Resource provisioning 481 provides dynamic procurement of computing resources and other resources that are utilized to perform tasks within the cloud computing environment. Metering and Pricing 482 provide cost tracking as resources are utilized within the cloud computing environment, and billing or invoicing for consumption of these resources. In one example, these resources may comprise application software licenses. Security 486 provides identity verification for cloud consumers and tasks, as well as protection for data and other resources. User portal 483 provides access to the cloud computing environment for consumers and system administrators. Service level management 484 provides cloud computing resource allocation and management such that required service levels are met. Service Level Agreement (SLA) planning and fulfillment 485 provide pre-arrangement for, and procurement of, cloud computing resources for which a future requirement is anticipated in accordance with an SLA.

Workloads layer 490 provides examples of functionality for which the cloud computing environment may be utilized. Examples of workloads and functions which may be provided from this layer include: mapping and navigation 491; software development and lifecycle management 492; virtual classroom education delivery 493; data analytics processing 494; transaction processing 495; aggregation and engines layer 220 (FIG. 2); and interaction layer 230 (FIG. 2).

Figure 5:
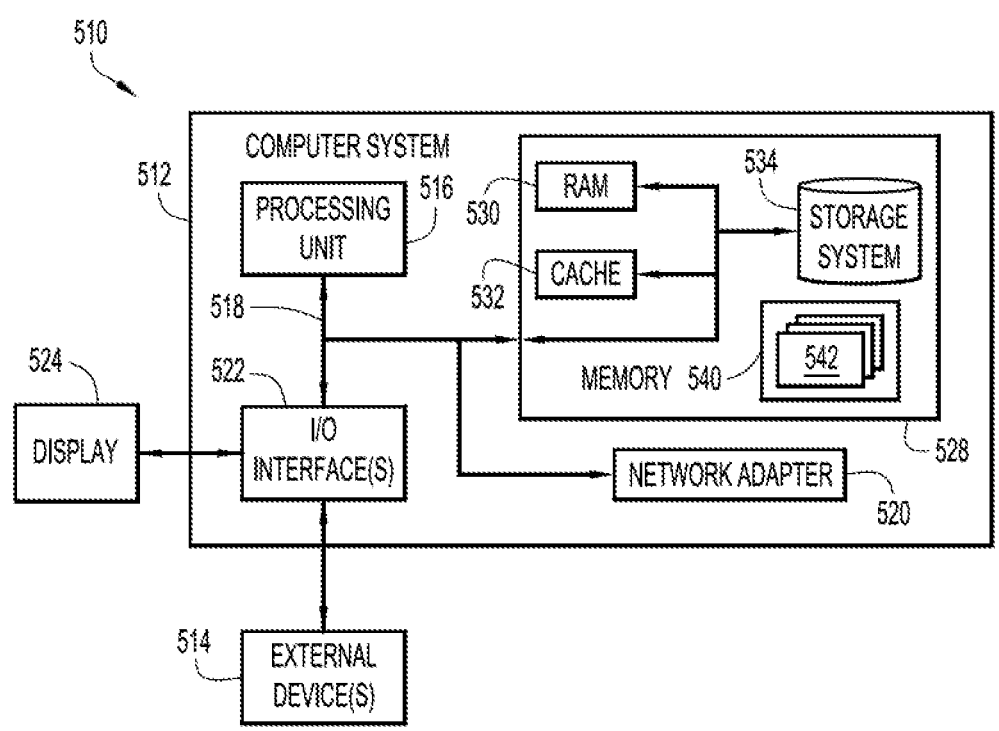
FIG. 5 is a block diagram of a computing node according to an embodiment of the present invention.

Referring now to FIG. 5, a schematic of an example of a computing node or device 510 of computer environment 100 (e.g., health data gateway 110, application server cluster 140, gateway controller 145, computing nodes of staging grid 150, computing nodes of factory grids 160, etc.) and cloud environment 350 (e.g., cloud computing node 310, etc.) is shown. The computing node or device is only one example of a suitable computing node for computing environment 100 and cloud computing environment 350 and is not intended to suggest any limitation as to the scope of use or functionality of embodiments of the invention described herein. Regardless, computing node 510 is capable of being implemented and/or performing any of the functionality set forth herein.

In computing node 510, there is a computer system 512 which is operational with numerous other general purpose or special purpose computing system environments or configurations. Examples of well-known computing systems, environments, and/or configurations that may be suitable for use with computer system 512 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 512 may be described in the general context of computer system executable instructions, such as program modules, being executed by a computer system. Generally, program modules may include routines, programs, objects, components, logic, data structures, and so on that perform particular tasks or implement particular abstract data types. Computer system 512 may be practiced in distributed cloud computing environments where tasks are performed by remote processing devices that are linked through a communications network. In a distributed cloud computing environment, program modules may be located in both local and remote computer system storage media including memory storage devices.

In FIG. 5, computer system 512 is shown in the form of a general-purpose computing device. The components of computer system 512 may include, but are not limited to, one or more processors or processing units 516, a system memory 528, and a bus 518 that couples various system components including system memory 528 to processor 516.

Bus 518 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 512 typically includes a variety of computer system readable media. Such media may be any available media that is accessible by computer system 512, and it includes both volatile and non-volatile media, removable and non-removable media.

System memory 528 can include computer system readable media in the form of volatile memory, such as random access memory (RAM) 530 and/or cache memory 532. Computer system 512 may further include other removable/non-removable, volatile/non-volatile computer system storage media. By way of example only, storage system 534 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 518 by one or more data media interfaces. As will be further depicted and described below, memory 528 may include at least one program product having a set (e.g., at least one) of program modules that are configured to carry out the functions of embodiments of the invention.

Program/utility 540, having a set (at least one) of program modules 542, may be stored in memory 528 by way of example, and not limitation, as well as an operating system, one or more application programs, other program modules, and program data. Each of the operating system, one or more application programs, other program modules, and program data or some combination thereof, may include an implementation of a networking environment. Program modules 542 generally carry out the functions and/or methodologies of embodiments of the invention as described herein.

Computer system 512 may also communicate with one or more external devices 514 such as a keyboard, a pointing device, a display 524, etc.; one or more devices that enable a user to interact with computer system 512; and/or any devices (e.g., network card, modem, etc.) that enable computer system 512 to communicate with one or more other computing devices. Such communication can occur via Input/Output (I/O) interfaces 522. Still yet, computer system 512 can communicate with one or more networks such as a local area network (LAN), a general wide area network (WAN), and/or a public network (e.g., the Internet) via network adapter 520. As depicted, network adapter 520 communicates with the other components of computer system 512 via bus 518. It should be understood that although not shown, other hardware and/or software components could be used in conjunction with computer system 512. Examples, include, but are not limited to: microcode, device drivers, redundant processing units, external disk drive arrays, RAID systems, tape drives, and data archival storage systems, etc.

Figure 6:
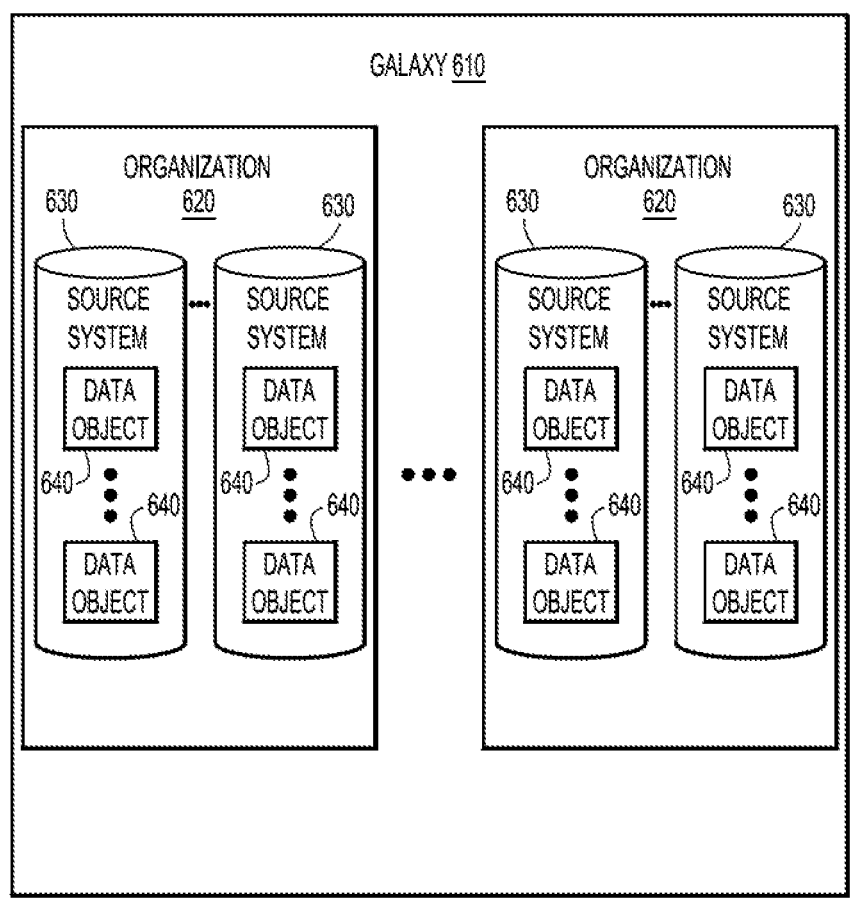
FIG. 6 is a block diagram illustrating the organization of data objects in a healthcare computing system according to an embodiment of the present invention.
Figure 7:
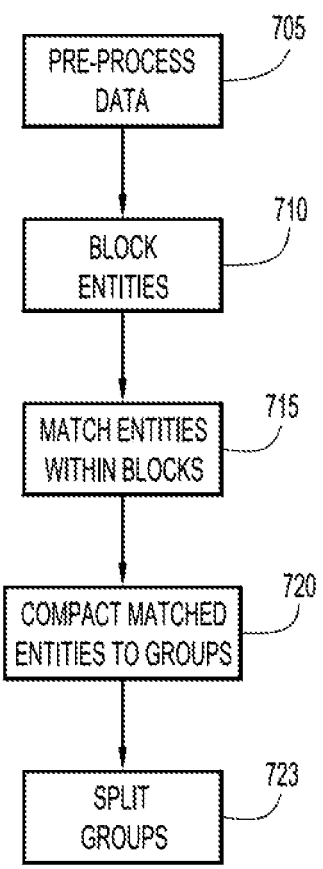
FIG. 7 is a procedural flowchart illustrating a manner of associating patient records with a common patient according to an embodiment of the present invention.

A manner of associating or linking records of a common patient or other entity (e.g., via the factory grid and patient matching module 264) is illustrated in FIGS. 6 and 7. Initially, data objects 640 may be distributed within a source system 630 of an organization 620 (which may in turn be part of a galaxy 610). By way of example, each source system 630 contains medical or other records associated with patients. For example, source systems 630 may correspond to source systems 125 described above (FIG. 2). However, source systems 630 may contain any types of records, and the system may identify records associated with any type of desired entity (e.g., person, corporate or other business entity, healthcare or other medical related entity, healthcare provider, etc.) in substantially the same manner described below.

Patient matching is then performed for each source system 630 to match patient records within that source system and determine the records associated with the same or common patient. The patient matching process may employ various matching algorithms to determine for each patient of a source system 630 a group of records of the source system associated with that patient. The patient matching process includes a data pre-processing stage, a blocking stage, a matching stage, a compaction stage, and a splitting stage. By way of example, each of these stages may be performed as a respective MapReduce job within the distributed computing environment of factory grid 160 (FIG. 2). However, present invention embodiments are environment agnostic and may be implemented in a non-distributed setting.

Referring to FIG. 7, patient records of each source system 630 are processed to perform patient matching to produce groups of patient records associated with the same or common patient. In particular, patient records of a source system 630 are retrieved and pre-processed at step 705. This includes cleaning and standardizing data within the retrieved patient records. For example, the data may be analyzed to identify: invalid social security numbers or other identifiers; invalid addresses and telephone numbers; and/or default values (e.g., a Birth date of 1900 Jan. 1 (year/month/day), etc.). Further, the data of the retrieved patient records is standardized to enable accurate comparisons of the data for patient matching (e.g., providing social security numbers in a desired format (e.g., with or without hyphens), providing data in corresponding fields (e.g., middle names in a first name or other field), etc.).

The resulting clean and standardized data is evaluated to arrange records of potentially matching patients into blocks at step 710. Each block contains records of patients that are sufficiently similar in order to compare records of those patients to each other in a pairwise fashion for associating the records with a common patient. Since the amount of patient records in the source systems is voluminous, comparing all pairs of patient records is impractical. For example, the amount of comparisons is proportional to the square of the number of records (e.g., $N^2$ comparisons are performed for N patient records). Thus, one trillion comparisons are performed for one million patient records. This task becomes burdensome and time consuming even within a distributed computing environment.

Reducing the number of comparisons is necessary to enhance computer processing performance, reduce processing time, and reduce certain types of errors. This is accomplished by organizing the collection of patient records into subsets or blocks. Each block contains patient records of patients that are sufficiently similar, where the records of those patients within the blocks are compared to reduce the overall number of comparisons.

The blocks are formed by comparing one or more fields of patient records to desired criteria. Exact matches on particular fields define blocks of patient records for pairwise comparisons of those records within each block (e.g., comparisons for social security number (SSN), medical record number (MRN), enterprise master patient index (EMPI), telephone number, phonetic name matching, etc.). This enables the pairwise comparisons of patient records to be limited to the patient records within the blocks (which are likely to be associated with the same or common patient), thereby reducing the overall number of patient record comparisons.

Various blocking schemes (e.g., criteria or combinations of record fields) may be utilized for the record comparisons to form the blocks of patient records. Thus, a single patient may be assigned to a plurality of different blocks based on the blocking schemes utilized for those blocks (e.g., combination of fields utilized for comparison of the patient records). The blocking schemes may include any quantity of any fields of the patient records for the record comparisons to form the blocks.

Once the blocks of patient records are formed, the patient records within each block are analyzed on an individual block basis to determine patient records associated with the same or common patient at step 715. The patient records within a block are compared to each other in a pairwise fashion to determine a likelihood score for the pair of records. The comparisons are limited to the patient records within the individual blocks in order to reduce the overall number of record comparisons as described above. When the likelihood score exceeds a similarity threshold, the patient records are linked and associated with the same patient.

In particular, the likelihood score is computed for a pair of patient records in a block to indicate the likelihood that the two patient records are associated with the same or common patient. The determination of the likelihood score for a pair of patient records is based on evidence from various "static" features or record fields that include data that is unlikely to change over time (e.g., first name, middle name/initial, last name, gender, birth year, birth month/day, social security number (SSN), medical record number (MRN), enterprise master patient index (EMPI), address, postal code, telephone number, etc.) and "temporal" features or record fields that include data describing characteristics that are likely to change over time (i.e., status of illness, medical schedule, height, weight, abilities, etc.). In other words, the likelihood score may be based on at least static information and supplemental temporal information. Moreover, in some embodiments, supplemental features that are non-temporal may also be considered together with or in view of the static and temporal information. For example, if a static feature indicates that a patient is a male and supplemental information for another patient indicates that a hysterectomy was performed, these two patients are unlikely to be the same patient, regardless of the date of the hysterectomy.

In embodiments specifically relating to patient matching, the supplemental temporal information includes healthcare information, which may include clinical information pertaining to one or more from a group of diagnoses, medications, vitals, lab tests, genomics, and medical procedures. The non-temporal supplemental information may also relate to healthcare information, but may be independent of time, perhaps simply indicating procedures performed, data relating to blood or vitals, genomics, etc.

Each feature is associated with different matching levels for a comparison. Each matching level for a feature comparison has a corresponding associated weight. The associated weights for the matching levels indicate a likelihood the patient records are associated with the same or common patient based on the level of matching of the corresponding feature or record field. The weights for the matches may be added to produce the likelihood score. When the likelihood score is greater than the similarity threshold, the patient records are linked and associated with the same patient. If the likelihood score is less than a difference threshold, the patient records are split or disassociated with one another (since the patient records reside in the same block).

Higher valued weights (and hence, a higher likelihood score) may indicate a greater likelihood of the patient records being associated with the same or common patient. However, the magnitude of the weight values (and likelihood score) may be associated with any desired degree of likelihood of association of the patient records with a common patient (e.g., greater likelihood, less likelihood, etc.). In addition, the similarity and difference thresholds may be set to any desired values to control the sensitivity or degree of matching needed to associate or link patient records with a common patient.

By way of example, some static features may be associated with different matching levels as follows:

a name feature (e.g., first name, middle name, last name, etc.) may be associated with matching levels of exact match, alias (nickname) match, phonetic match, typographical (error) match, and a transpose match;

a birth date feature may be associated with matching levels of exact match, typographical match, and a transpose match;

a patient identifiers feature may be associated with a matching level of an exact match for social security number (SSN), medical record number (MRN), enterprise master patient index (EMPI), etc.;

a telephone number feature may be associated with matching levels of an exact match and a typographical match;

an address feature may be associated with matching levels of an exact match, a typographical match, and a distance match (e.g., addresses within a threshold quantity of miles, etc.); and an electronic (Email) mail address feature may be associated with matching levels of an exact match, and a typographical match.

Temporal information may used to supplement the static information in order to account for features that are not yet accounted for in the likelihood score. Although temporal features must be considered in view of time, temporal features may still result in different matching levels that can either impact the likelihood score subsequent to its generation based on the static information or be considered in the generation of the likelihood score. For example:

a height feature may be associated with matching levels of an exact match, a reasonable match, and an unreasonable match, depending on known growth rates and the time lapsed between height measurements; and a weight feature may be associated with matching levels of an exact match, a reasonable match, and an unreasonable match, depending on age, health factors, time lapsed between the weight measurements, and other such considerations.

In some embodiments, the temporal information may prevent and/or substantially discourage a match from being found by applying a substantial penalty to the likelihood score. Alternatively, the temporal information may confirm a match and/or increase the likelihood score. In some embodiments, temporal information may require input from subject matter experts in order to be given the appropriate weight. For example, the supplemental temporal information may include clinical information and, in view of knowledge of the particular clinical subject (i.e., time-based medical knowledge, such as knowledge of how much a person typically grows over a certain amount of time, or the time intervals at which a person with a particular disease will be required to receive a particular treatment), this clinical information may indicate whether the candidate objects can or are likely to be associated with the common entity. In other words, temporal information may be evaluated in view of a set of rules or policies in order to supplement the static information.

As a more specific example, if two records for John Smith with the same birthday appear in a source system, the height measurements taken for each John Smith may be compared. If the first John Smith was 6'4 on Apr. 1, 2015, and the second John Smith was 5'4 on Mar. 15, 2015, the system may determine that this is an unreasonable match if a subject matter expert had previously indicated that growing one foot in one month is extremely unlikely, even during a growth spurt. In this situation, a negative penalty can be applied to the likelihood score, reducing the chance of the likelihood score exceeding the threshold and indicating a match. If instead, the patient records are both for John Smith, who is age 17, but have height differences of 6 inches over a year; this height difference may be given minimal weight since seventeen year olds frequently have growth spurts. For example, an extremely small penalty may be applied to the likelihood score, supplementing the static information. In order to obtain these different outcomes, a subject matter expert would be required to input rules indicating which height patterns are reasonable and which height patterns are unreasonable, perhaps along a scale.

As another example, if two records for Jane Doe have nearly identical static information (i.e., birthday and name), but one record for Jane Doe indicates that Jane Doe gave birth on Jun. 1, 2015, and the other record indicates that Jane Doe had a hysterectomy procedure on Jun. 1, 2014, a large penalty may be applied to the likelihood score since a hysterectomy may prevent births on dates subsequent to the surgery date. Alternatively, a match may be prevented from being found. However, since a record with a hysterectomy is not always restricted from matching with a record for a birth (i.e., the birth may come first), a subject matter expert may be required to input a rule indicating that records indicating a hysterectomy are extremely unlikely to be matched to records indicating births only if the birth is subsequent to the hysterectomy. In other words, since there is no clinical knowledge that would link a patient record for delivery of a child with a patient record for a hysterectomy that occurred subsequent to the child delivery, not all records for hysterectomies impact whether or not the patient records are associated with a common entity and this must be accounted for in the rule.

As still another example, kidney failure may require a patient to receive dialysis resulting in regular visits to a physician's office subsequent to the kidney failure but not necessarily prior to the kidney failure. Consequently, a patient record indicating kidney failure should likely not be matched with a patient record indicating infrequent visits to the physician's office subsequent to the date of kidney failure. However, a patient with frequent visits to the physician's office prior to the kidney failure would not have any impact on the likelihood score. The timing and clinical information are important factors when considering supplemental temporal information and, thus, must be accounted for by rules created with input from subject matter experts.

However, temporal information need not only be used to apply penalties to likelihood scores. In some instances, if multiple patient records indicate a rare or very specific medical procedure (i.e., a left foot amputation occurred on Feb. 1, 2013), the likelihood score for these two medical records may be increased or a match may be confirmed. In fact, in some situations, a rare procedure occurring on a specific data may overrule or outweigh the impact of static information that is only slightly different. For example, if a first record included a patient name of John Smith, a birth date of Jan. 1, 1978 (i.e. 1978-01-01), and a left foot amputation on Feb. 1, 2012, while a second record included a patient name of Jon Smith, a birth date of Jan. 10, 1978 (i.e., 1978-01-10), and a left foot amputation on Feb. 1, 2012, the match for the amputation may cause these records to be considered a match (i.e., have a likelihood score above the threshold) despite the lack of exact matches in the static information. In other words, an exact match in temporal information may, in some embodiments, overrule or outweigh static features indicating that a match is unlikely.

In different embodiments, different criteria or rules specifying additional temporal information to retrieve may be utilized. Moreover, in different embodiments, a match between temporal information may be given a different weight or impact. For example, if a system has extremely high quality data (i.e., highly accurate, minimal typographical errors, and minimal incorrect entries), the temporal information may be given great weight and may prevent or cause match irrespective of the static data. However, if a system has data of questionable quality, the temporal information may be given minimal weight and simply be considered as another input in the likelihood score. In view of this, the rules and criteria for temporal information may be highly configurable depending on the organization 630 or source system 620 from which the data objects 340 (i.e., patient records) are retrieved.

By way of example, some rules may determine whether temporal information creates a conflict (which may lower the overall likeness score), provides no information (which has no impact on the likeness score), or indicates a match (which may raise the overall likeness score) and may be implemented as follows:

For the hysterectomy example discussed above:

```
if patient 1 had hysterectomy:
    if patient 2 gave birth after patient 1s hysterectomy:
        return CONFLICT;
if patient 2 had hysterectomy:
    if patient 1 gave birth after patient 2s hysterectomy:
        return CONFLICT;
return NO_INFORMATION;
```

Similarly, for the dialysis example discussed above:

```
if (patient 1 last dialysis date < patient 2 first dialysis date) OR (patient 2 last dialysis date < patient 1 first dialysis date):
    return MATCH
return NO_INFORMATION
```

Still referring to FIG. 7, patient matching compares patient records within a block to each other in a pairwise fashion, and links records together based on the result of the comparison. Thus, various pairs of patient records may be linked to one another based on the comparisons within the blocks. For example, a patient record within a plurality of blocks may be linked to multiple records from among those plurality of different blocks. The linked patient records are processed to transform pairs of linked patient records into groups of patient records 640 (FIG. 6) associated with a common patient at step 720.

The linked pairs of patient records may be represented graphically (FIGS. 8A-8F), and combined or compacted to form groups of patient records with each group associated with a corresponding patient. In this case, a connected components process is employed on the graphical representation of the linked patient records to convert the graphical representation into all disjoint subgraphs in order to determine the groups.

Figure 8A:
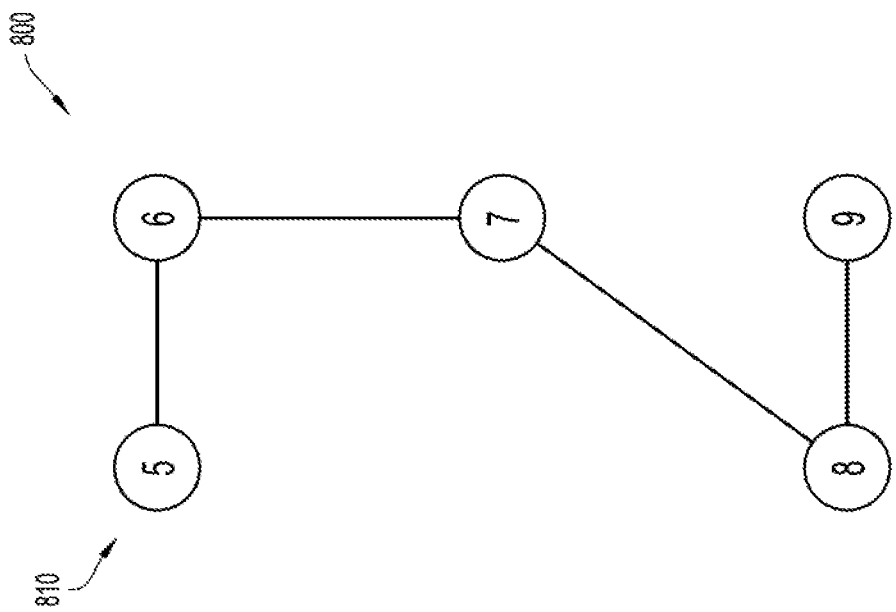
FIG. 8A is a diagrammatic illustration of an example graphical representation of linked patient records.
Figure 8A:
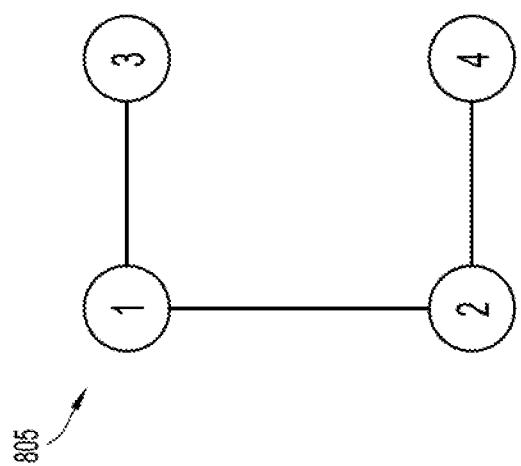

The connected components process is iterative and passes information pertaining to connectedness throughout the graphical representation. By way of example, a graphical representation 800 of linked patient records is illustrated in FIG. 8A. The graphical representation includes vertices representing patient records 1-9. The edges between the vertices indicate a link between patient records based on the patient matching described above.

The links or connections between vertices or patient records are indicated by a table 820a (FIG. 8B). The table includes, by way of example, a row for each vertex or patient record and columns for: the vertex identifier (e.g., 1-9 as shown in FIG. 8A); vertex identifiers for adjacent vertices; an assigned group identifier; and an activated status (e.g., True or False). Initially, each vertex has an assigned group identifier set to a minimum of the vertex identifier of that vertex and the vertex identifiers of adjacent vertices.

Table 820a indicates the initial connections, assigned group identifiers, and activated status for graphical representation 800. For example: vertex 1 is connected to vertices 2, 3, and has a group identifier set to the minimum vertex identifier of 1; vertex 2 is connected to vertices 1, 4, and has a group identifier set to the minimum vertex identifier of 1; vertex 3 is connected to vertex 1, and has a group identifier set to the minimum vertex identifier of 1; vertex 4 is connected to vertex 2, and has a group identifier set to the minimum vertex identifier of 2; vertex 5 is connected to vertex 6, and has a group identifier set to the minimum vertex identifier of 5; vertex 6 is connected to vertices 5, 7, and has a group identifier set to the minimum vertex identifier of 5; vertex 7 is connected to vertices 6, 8, and has a group identifier set to the minimum vertex identifier of 6; vertex 8 is connected to vertices 7, 9, and has a group identifier set to the minimum vertex identifier of 7; and vertex 9 is connected to vertex 8, and has a group identifier set to the minimum vertex identifier of 8. In addition, the activated status for each vertex is initially set to True.

Each activated vertex (e.g., a vertex with an activated status of True) passes the assigned group identifier of that vertex to corresponding adjacent vertices. The assigned group identifier for each of the adjacent vertices is updated to be the minimum of the current assigned group identifier for that adjacent vertex and the group identifiers passed to that adjacent vertex. By way of example with respect to graphical representation 800: the assigned group identifier for vertex 4 is updated from group identifier 2 to group identifier 1 (e.g., minimum of vertex group identifier 2 and passed group identifier 1 (from vertex 2)); the assigned group identifier for vertex 7 is updated from group identifier 6 to group identifier 5 (e.g., minimum of vertex group identifier 6 and passed group identifiers 5 (from vertex 6) and 7 (from vertex 8)); the assigned group identifier for vertex 8 is updated from group identifier 7 to group identifier 6 (e.g., minimum of vertex group identifier 7 and passed group identifiers 6 (from vertex 7) and 8 (from vertex 9)); and the assigned group identifier for vertex 9 is updated from group identifier 8 to group identifier 7 (e.g., minimum of vertex group identifier 8 and passed group identifier 7 (from vertex 8)). In addition, vertices with changed group assignments have an activated status set to True, while remaining vertices have an activated status set to False. These changes (or iteration of the process) are reflected in connection table 820b (FIG. 8C).

Each activated vertex (e.g., a vertex with an activated status of True) from table 820b passes the assigned group identifier of that vertex to corresponding adjacent vertices. The assigned group identifier for each of the adjacent vertices is updated to be the minimum of the current assigned group identifier for that adjacent vertex and the group identifiers passed to that adjacent vertex. By way of example with respect to graphical representation 800 and table 820*b*: the assigned group identifier for vertex 8 is updated from group identifier 6 to group identifier 5 (e.g., minimum of vertex group identifier 6 and passed group identifiers 5 (from vertex 7) and 7 (from vertex 9)); and the assigned group identifier for vertex 9 is updated from group identifier 7 to group identifier 6 (e.g., minimum of vertex group identifier 7 and passed group identifier 6 (from vertex 8)). In addition, vertices with changed group assignments have an activated status set to True, while remaining vertices have an activated status set to False. These changes (or iteration of the process) are reflected in connection table 820*c* (FIG. 8D).

Each activated vertex (e.g., a vertex with an activated status of True) from table 820*c* passes the assigned group identifier of that vertex to corresponding adjacent vertices. The assigned group identifier for each of the adjacent vertices is updated to be the minimum of the current assigned group identifier for that adjacent vertex and the group identifiers passed to that adjacent vertex. By way of example with respect to graphical representation 800 and table 820*c*: the assigned group identifier for vertex 9 is updated from group identifier 6 to group identifier 5 (e.g., minimum of vertex group identifier 6 and passed group identifier 5 (from vertex 8)). In addition, vertices with changed group assignments have an activated status set to True, while remaining vertices have an activated status set to False. These changes (or iteration of the process) are reflected in connection table 820*d* (FIG. 8E).

Each activated vertex (e.g., a vertex with an activated status of True) from table 820*d* passes the assigned group identifier of that vertex to corresponding adjacent vertices. Since no further changes to assigned group identifiers occurs, all vertices are inactive (e.g., activated status set to False) and the process has converged. The final groups are reflected in table 820*e* (FIG. 8F), where graphical representation 800 includes a group 805 of vertices 1-4 with an assigned group identifier of 1, and a group 810 of vertices 5-9 with an assigned group identifier of 5. The corresponding patient records within each group are linked together to indicate the association with the same or common patient.

Figure 9:
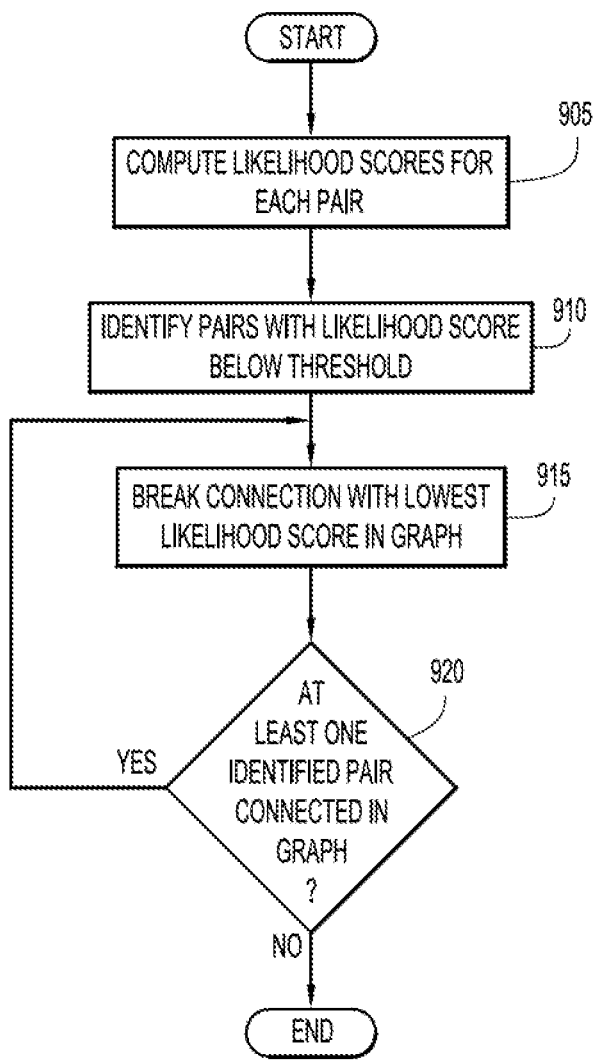
FIG. 9 is a procedural flowchart illustrating a manner of splitting a group of associated patient records according to an embodiment of the present invention.
Figure 10C:
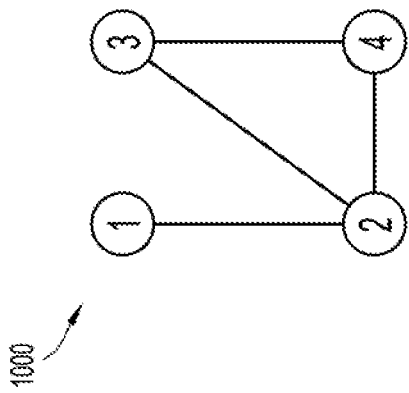
FIGS. 10A-10E are diagrammatic illustrations of example graphical representations of a group of linked patient records being split into plural groups according to an embodiment of the present invention.
Figure 10B:
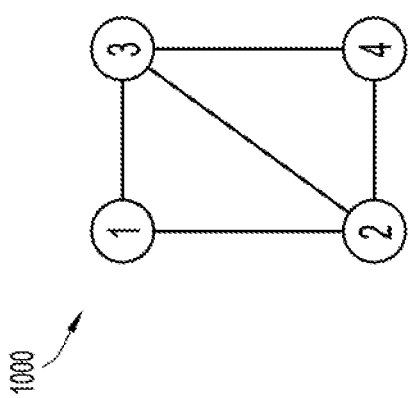
Figure 10A:
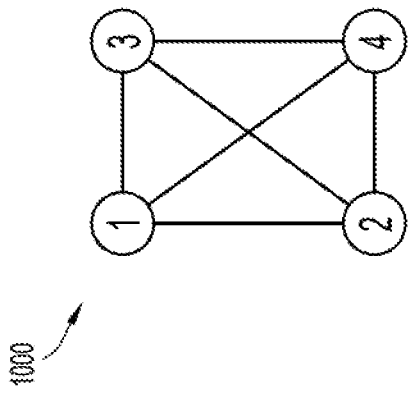
Figure 10E:
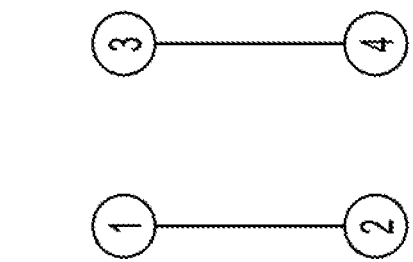
Figure 10D:
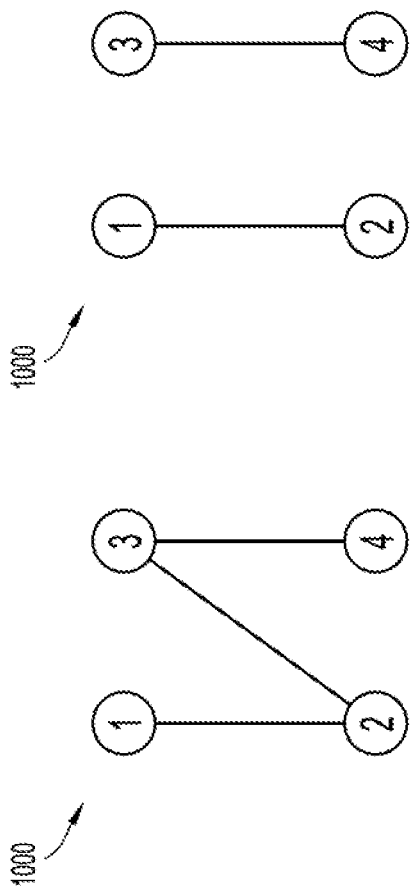

The patient records within each resulting group are subsequently examined at step 723 to split that group into a plurality of groups as illustrated in FIG. 9. This analysis compensates for errors due to transitivity (e.g., patient record A is linked to patient record C since patient record A is linked to patient record B and patient record B is linked to patient record C). For example, two patient records within a group may have different social security numbers. In this case, the group would be split into different groups separating the two patient records (and corresponding patients).

Initially, all patient records within a group are compared in a pairwise fashion at step 905 to produce a likelihood score for the pair as described above. For example, weights are associated for matching levels of features, including static and temporal features, and indicate a likelihood the patient records are associated with the same or common patient. The weights for matches between the pair of patient records may be added to produce the likelihood score based on the level of matching of the corresponding features or record fields. The resulting likelihood scores for the patient records are compared to a splitting threshold to identify pairs of patient records with a likelihood score below the splitting threshold at step 910.

The group of patient records may be represented graphically, where vertices represent the patient records and each edge between a pair of vertices or patient records is associated with a corresponding likelihood score for that pair. Initially, the graphical representation includes edges between each pair of patient records in the group. The edge between patient records associated with the lowest likelihood score is removed from the graphical representation at step 915. The graphical representation is examined to determine whether the records of each of the identified pairs of patient records (with a likelihood score below the splitting threshold) remain connected after removal of the edge. This may be accomplished by applying a conventional or other shortest path algorithm to determine a shortest path between the patient records of the identified pairs. When records of at least one of the identified pairs of patient records remain connected within the graphical representation as determined at step 920 (e.g., a shortest path can be determined between the patient records of at least one identified pair), the above process is repeated from step 915 by removing the edge between patient records associated with the next lowest likelihood score. The process continues until no connections exist in the graphical representation between the records of each of the identified pairs of patient records.

Thus, the splitting process iteratively breaks the weakest edges (e.g., associated with the lowest likelihood scores) until there are no connections between the identified pairs of patient records with likelihood scores below the splitting threshold. In other words, there are no edges in the graphical representation of the group with likelihood scores below the splitting threshold. The resulting groups after the removal of edges are provided as the groups of patient records 640 associated with common patients.

By way of example and referring to FIGS. 10A-10E, a group may include four patient records (e.g., patient record 1 to patient record 4), where the likelihood score for patient records 1 and 3, and patient records 1 and 4 are below the splitting threshold. Initially, the graphical representation 1000 of the group (FIG. 10A) includes edges between each pair of vertices or records in the group (e.g., between patient record 1 and patient records 2, 3, and 4; between patient record 2 and patient records 3 and 4; and between patient record 3 and patient record 4). The edge between patient records 1 and 3 in the graphical representation of the group is initially removed (since this pair is associated with the lowest likelihood score) (FIG. 10B), and a shortest path algorithm is utilized to determine whether connections remain between patient record 1 and patient records 3 and 4 (e.g., with likelihood scores below the splitting threshold). Since connections remain between patient record 1 and patient records 3 and 4, the process is repeated by iteratively removing the edges (which are associated with the next lowest likelihood scores in this example) between patient records 1 and 3 (FIG. 10C), between patient records 2 and 4 (FIG. 10D), and between patient records 2 and 3 (FIG. 10E) to produce a resulting graphical representation (FIG. 10E) with no connections between patient record 1 and patient records 3 and 4 (e.g., associated with likelihood scores below the splitting threshold). The resulting graphical representation provides disjoint groups including a first group with patient records 1 and 2, and a second group with patient records 3 and 4, where each group is associated with a different patient.

It will be appreciated that the embodiments described above and illustrated in the drawings represent only a few of the many ways of implementing embodiments for association of entity records based on supplemental temporal information.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, patient matching module, etc.). These systems may include any types of monitors and input devices (e.g., keyboard, mouse, voice recognition, etc.) to enter and/or view information.

It is to be understood that the software (e.g., patient matching module, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., patient matching module, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., blocking or matching criteria, thresholds, etc.). The database system may be implemented by any number of any conventional or other databases, data stores or storage structures (e.g., files, databases, data structures, data or other repositories, etc.) to store information. The database system may be included within or coupled to the server and/or client systems. The database systems and/or storage structures may be remote from or local to the computer or other processing systems, and may store any desired data.

The present invention embodiments may utilize data in any desired structure (e.g., records, data objects, data structures, etc.), and associate the data with any desired entity (e.g., person, corporate or other business entity, healthcare or other medical related entity, healthcare provider, etc.).

The blocking scheme may arrange any quantity or unit of records (e.g., individual records, groups of records, sets of groups, collections of sets, etc.) into blocks or sub-groups for comparisons based on any desired criteria (e.g., any type of matching of any portion of any quantity of record fields, based on record characteristics, etc.). Any quantity of records within a unit (e.g., group of records, sets of groups, collection of sets, etc.) may match the criteria in any fashion to qualify for a block. The similarity and difference thresholds may be set to any desired values.

The matching process may compare or match any quantity of records (e.g., individual records, groups of records, sets of groups, collections of sets, etc.) based on any desired criteria (e.g., any quantity or combination of record fields or features, etc.). Further, the matching criteria may be expanded in any fashion to account for additional information (e.g., increase variants or values provided for matching, expand matching types or levels, etc.). The likelihood score may include any quantity of any types of levels of matching (e.g., exact, partial, phonetic, typo, etc.). The weights may be assigned to the matching levels in any desired fashion, and include any values. The matching level associated with any desired weight (e.g., greatest weight, lowest weight, etc.) may be selected for a feature of a plurality of records (e.g., group of records, set of groups, collection of sets, etc.). The weights may be combined in any fashion to provide a likelihood score. The value of the likelihood score may be associated with any degree of similarity (e.g., a lesser likelihood score may indicate a greater chance for a match, a greater likelihood score may indicate a greater chance for a match, etc.).

The linked units (e.g., linked records) may be represented graphically in any fashion (e.g., nodes and edges or arcs, etc.). The disjoint sets within the graphical representation (e.g., linked records) may be identified in any fashion. The splitting may split a group of records into any quantity of those units based on any desired criteria (e.g., high or low likelihood values, any suitable matching criteria, etc.). The splitting threshold may be set to any desired value.

Records may be associated with the resulting entity based on any data (e g, linking the actual records (e.g., pointer or other indicator, etc.), grouping record or other identifiers to associate the records with a entity, etc.). The process may include one or more from a group of the pre-processing, blocking, matching, compaction, and splitting stages, either individually or any combination.

The present invention embodiments may employ any number of any type of user interface (e.g., Graphical User Interface (GUI), command-line, prompt, etc.) for obtaining or providing information (e.g., queries, analytic results, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The present invention embodiments are not limited to the specific tasks or algorithms described above, but may be utilized for associating data from various data systems with any type of common entity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method of linking data objects associated with a common entity comprising:
    arranging data objects into blocks by comparing one or more fields of the data objects to corresponding criteria for the blocks, wherein at least one data object is assigned to a plurality of different blocks and each block corresponds to a different entity and contains data objects associated with that different entity;
    comparing within the blocks the fields of the data objects to each other to identify candidate data objects with one or more matching fields and associated with a corresponding common entity;
    analyzing supplemental temporal information within the candidate data objects to confirm that the candidate data objects are associated with the common entity;
    linking the candidate data objects that are confirmed to be associated with the common entity to form a set of data objects for the common entity; and
    processing a query for an entity to retrieve data from a corresponding set of data objects for that entity.

2. The computer-implemented method of claim 1, wherein the supplemental temporal information includes healthcare information.

3. The computer-implemented method of claim 2, wherein the healthcare information includes clinical information pertaining to one or more from a group of diagnoses, medications, vitals, lab tests, genomics, and medical procedures.

4. The computer-implemented method of claim 1, wherein the common entity includes a patient.

5. The computer-implemented method of claim 1, wherein analyzing the supplemental temporal information includes:
    applying one or more rules specifying how to utilize the supplemental temporal information to confirm the candidate data objects.

6. The computer-implemented method of claim 1, wherein analyzing the supplemental temporal information includes:
    removing one or more candidate data objects based on the supplemental temporal information disassociating the one or more candidate data objects with the common entity.

7. The computer-implemented method of claim 1, wherein the supplemental temporal information includes clinical information that indicates whether the candidate data objects are associated with the common entity in view of time-based medical knowledge.

8. A system for linking data objects associated with a common entity comprising:
    at least one processor configured to:
        arrange data objects into blocks by comparing one or more fields of the data objects to corresponding criteria for the blocks, wherein at least one data object is assigned to a plurality of different blocks and each block corresponds to a different entity and contains data objects associated with that different entity;
        compare within the blocks the fields of the data objects to each other to identify candidate data objects with one or more matching fields and associated with a corresponding common entity;
        analyze supplemental temporal information within the candidate data objects to confirm that the candidate data objects are associated with the common entity;
        link the candidate data objects that are confirmed to be associated with the common entity to form a set of data objects for the common entity; and
        process a query for an entity to retrieve data from a corresponding set of data objects for that entity.

9. The system of claim 8, wherein the supplemental temporal information includes healthcare information.

10. The system of claim 9, wherein the healthcare information includes clinical information pertaining to one or more from a group of diagnoses, medications, vitals, lab tests, genomics, and medical procedures.

11. The system of claim 8, wherein the common entity includes a patient.

12. The system of claim 8, wherein analyzing the supplemental temporal information includes:

applying one or more rules specifying how to utilize the supplemental temporal information to confirm the candidate data objects.

13. The system of claim 8, wherein analyzing the supplemental temporal information includes:
removing one or more candidate data objects based on the supplemental temporal information disassociating the one or more candidate data objects with the common entity.

14. The system of claim 8, wherein the supplemental temporal information includes clinical information that indicates whether the candidate data objects are associated with the common entity in view of time-based medical knowledge.

15. A computer program product for linking data objects associated with a common entity, the computer program product comprising a computer readable storage medium having program instructions embodied therewith, the program instructions executable by at least one processor to cause the at least one processor to:
arrange data objects into blocks by comparing one or more fields of the data objects to corresponding criteria for the blocks, wherein at least one data object is assigned to a plurality of different blocks and each block corresponds to a different entity and contains data objects associated with that different entity;
compare within the blocks the fields of the data objects to each other to identify candidate data objects with one or more matching fields and associated with a corresponding common entity;
analyze supplemental temporal information within the candidate data objects to confirm that the candidate data objects are associated with the common entity;
link the candidate data objects that are confirmed to be associated with the common entity to form a set of data objects for the common entity; and
process a query for an entity to retrieve data from a corresponding set of data objects for that entity.

16. The computer program product of claim 15, wherein the supplemental temporal information includes healthcare information.

17. The computer program product of claim 16, wherein the healthcare information includes clinical information pertaining to one or more from a group of diagnoses, medications, vitals, lab tests, genomics, and medical procedures.

18. The computer program product of claim 15, wherein the common entity includes a patient.

19. The computer program product of claim 15, wherein analyzing the supplemental temporal information further comprises one or more from a group of:
applying one or more rules specifying how to utilize the supplemental temporal information to confirm the candidate data objects; and
removing one or more candidate data objects based on the supplemental temporal information disassociating the one or more candidate data objects with the common entity.

20. The computer program product of claim 15, wherein the supplemental temporal information includes clinical information that indicates whether the candidate data objects are associated with the common entity in view of time-based medical knowledge.

* * * * *